US012350391B2

(12) United States Patent
Saito et al.

(10) Patent No.: US 12,350,391 B2
(45) Date of Patent: Jul. 8, 2025

(54) PROCESSING DEVICE, UV EMISSION DEVICE, AND UV EMISSION METHOD

(71) Applicant: DAIKIN INDUSTRIES, LTD., Osaka (JP)

(72) Inventors: Tomoki Saito, Osaka (JP); Toshio Tanaka, Osaka (JP); Kiyoshi Kuroi, Osaka (JP); Mamoru Okumoto, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 18/374,501

(22) Filed: Sep. 28, 2023

(65) Prior Publication Data

US 2024/0016963 A1  Jan. 18, 2024

Related U.S. Application Data

(63) Continuation of application No. PCT/JP2022/011746, filed on Mar. 15, 2022.

(30) Foreign Application Priority Data

Mar. 31, 2021 (JP) ................................. 2021-060751

(51) Int. Cl.
*A61L 2/10* (2006.01)
*A61L 2/24* (2006.01)

(52) U.S. Cl.
CPC .................... *A61L 2/10* (2013.01); *A61L 2/24* (2013.01); *A61L 2202/14* (2013.01)

(58) Field of Classification Search
CPC ........... A61L 2/10; A61L 2/24; A61L 2202/14
See application file for complete search history.

(56) References Cited

U.S. PATENT DOCUMENTS

2017/0112954 A1  4/2017 Dayton
2018/0110890 A1  4/2018 Matsui
(Continued)

FOREIGN PATENT DOCUMENTS

EP  3 290 058 A1  3/2018
EP  4 085 936 A1  9/2022
(Continued)

OTHER PUBLICATIONS

International Search Report of corresponding PCT Application No. PCT/JP2022/011746 dated May 24, 2022.
(Continued)

*Primary Examiner* — Sean E Conley
*Assistant Examiner* — Brendan A Hensel
(74) *Attorney, Agent, or Firm* — GLOBAL IP COUNSELORS, LLP

(57) ABSTRACT

A UV emission device includes an irradiator, a control unit, a determiner, and an exposure amount output unit. The irradiator irradiates a predetermined irradiation area in a predetermined space with ultraviolet rays. The control unit controls the irradiator based on a total exposure amount of a target person to ultraviolet rays. The determiner performs a determination process of determining whether or not the target person is present in the irradiation area. The exposure amount output unit outputs an amount of exposure of the target person to ultraviolet rays based on a determination result of the determiner and operation information on the irradiator. The control unit adds the amount of exposure of ultraviolet rays to the total exposure amount of ultraviolet rays in order to update the total exposure amount.

13 Claims, 11 Drawing Sheets

(56) References Cited

U.S. PATENT DOCUMENTS

| | | |
|---|---|---|
| 2018/0161468 A1 | 6/2018 | Dayton |
| 2019/0192710 A1 | 6/2019 | Andersson et al. |
| 2019/0351085 A1 | 11/2019 | Dayton |
| 2020/0254125 A1* | 8/2020 | Lloyd ................ A61L 2/10 |
| 2021/0015959 A1 | 1/2021 | Goseki et al. |
| 2022/0040344 A1 | 2/2022 | Okumura |
| 2022/0062452 A1 | 3/2022 | Okumura |
| 2022/0062463 A1* | 3/2022 | Ramer ............... H05B 47/16 |
| 2022/0184253 A1* | 6/2022 | Childress ............ A61L 2/24 |

FOREIGN PATENT DOCUMENTS

| | | |
|---|---|---|
| JP | 2009-14259 A | 1/2009 |
| JP | 2016-193059 A | 11/2016 |
| JP | 2017-533810 A | 11/2017 |
| JP | 2019-536492 A | 12/2019 |
| JP | 2019-537473 A | 12/2019 |
| JP | 2020-111369 A | 7/2020 |
| JP | 6908172 B1 | 7/2021 |
| JP | 6977853 B1 | 12/2021 |
| WO | 2019/186880 A1 | 10/2019 |
| WO | 2019/190967 A1 | 10/2019 |
| WO | 2021/202895 A1 | 10/2021 |
| WO | 2022/005507 A1 | 1/2022 |
| WO | 2022/190606 A1 | 9/2022 |

OTHER PUBLICATIONS

International Preliminary Report of corresponding PCT Application No. PCT/JP2022/011746 dated Oct. 12, 2023.
European Search Report of corresponding EP Application No. 22 78 0097.6 dated Jul. 8, 2024.

* cited by examiner

PROCESSING DEVICE, UV EMISSION DEVICE, AND UV EMISSION METHOD

CROSS-REFERENCE TO RELATED APPLICATIONS

This is a continuation of International Application No. PCT/JP2022/011746 filed on Mar. 15, 2022, which claims priority to Japanese Patent Application No. 2021-60751, filed on Mar. 31, 2021. The entire disclosures of these applications are incorporated by reference herein.

BACKGROUND

Technical Field

The present disclosure relates to a processing device, an ultraviolet (UV) emission device, and a UV emission method.

Background Art

An air conditioner described in Japanese Unexamined Patent Publication No. 2009-14259 includes an emitter means configured to emit ultraviolet rays into an installation space, an emission direction changing means configured to change the direction in which the ultraviolet rays are emitted, and a control means. If a moving body is present in the space, the control means controls the emission direction changing means to make the emitter means emit ultraviolet rays into the installation space without emission to the position of the moving body based on positional information on the moving body. Thus, ultraviolet rays can be emitted into a living space without emission to a moving body such as a human body or an animal.

SUMMARY

A first aspect of the present disclosure is directed to a UV emission device. The UV emission device includes an irradiator, a control unit, a determiner, and an exposure amount output unit. The irradiator is configured to irradiate a predetermined irradiation area in a predetermined space with ultraviolet rays. The control unit is configured to control the irradiator based on a total exposure amount of a target person to ultraviolet rays. The determiner is configured to perform a determination process of determining whether or not the target person is present in the irradiation area. The exposure amount output unit is configured to output an amount of exposure of the target person to ultraviolet rays based on a determination result of the determiner and operation information on the irradiator. The control unit is configured to add the amount of exposure of ultraviolet rays to the total exposure amount of ultraviolet rays in order to update the total exposure amount.

DETAILED DESCRIPTION OF EMBODIMENT(S)

Figure 1:
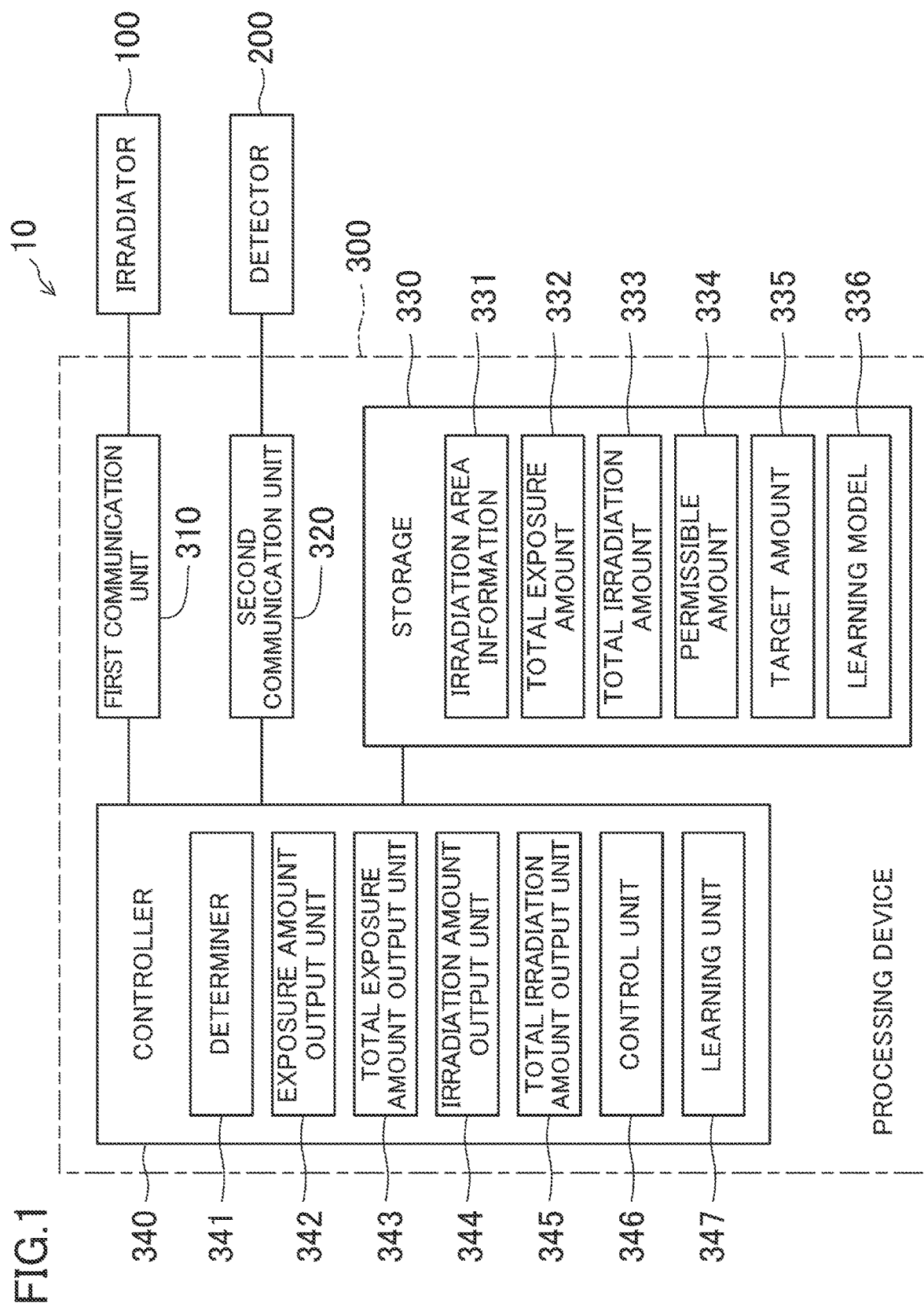
FIG. 1 is a block diagram illustrating a configuration of a UV emission device according to a first embodiment of the present invention.

Embodiments of the present invention will be described in detail with reference to the drawings. Note that like reference characters denote the same or equivalent components in the drawings, and the detailed description thereof, the description of advantages associated therewith, and other descriptions will not be repeated.

First Embodiment

Figure 2:
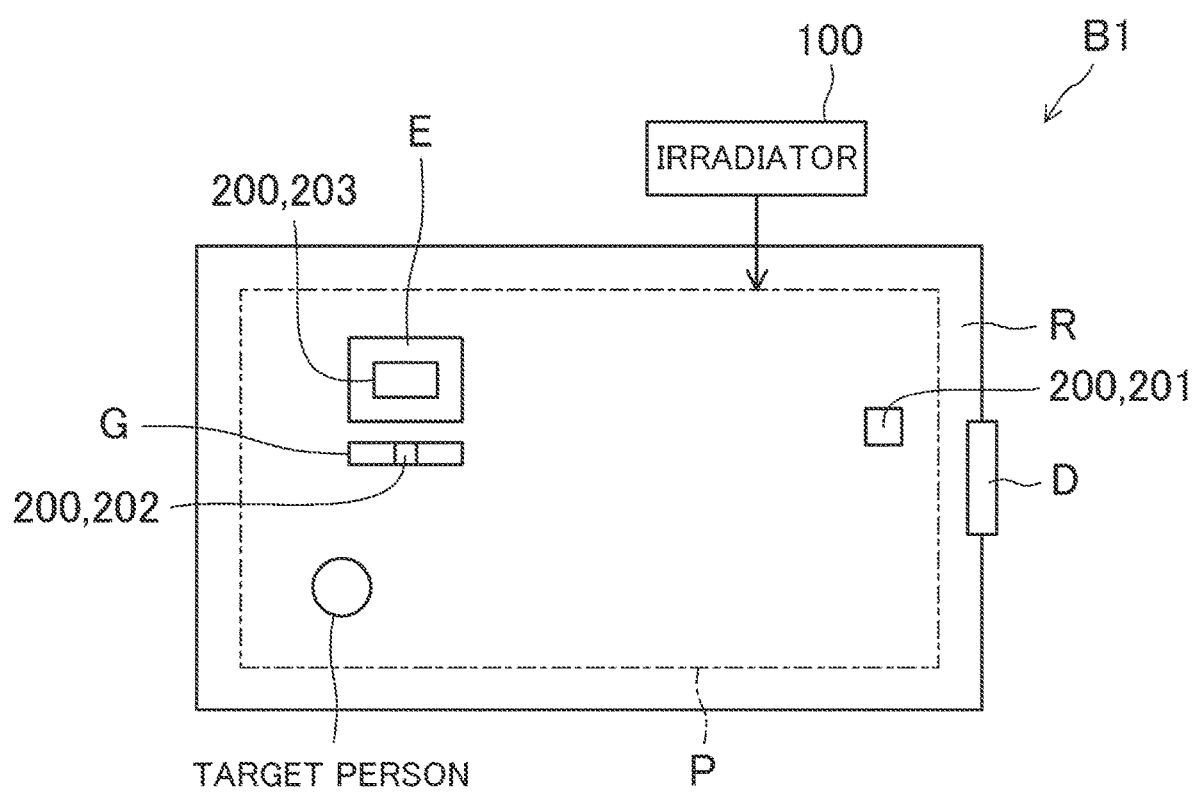
FIG. 2 illustrates a first example of installation of an irradiator and detectors.

A UV emission device (10) according to a first embodiment of the present invention will be described with reference to FIGS. 1 and 2. FIG. 1 is a block diagram illustrating a configuration of the UV emission device (10) according to the first embodiment of the present invention. FIG. 2 illustrates a first example of installation of an irradiator (100) and detectors (200).

General Configuration

As illustrated in FIGS. 1 and 2, the UV emission device (10) includes the irradiator (100), the detectors (200), and a processing device (300).

The irradiator (100) irradiates a predetermined irradiation area (P) in a predetermined space with ultraviolet rays. The ultraviolet rays emitted from the irradiator (100) have a wavelength greater than or equal to 190 nm and less than or equal to 280 nm, for example. Examples of the irradiator (100) include a light source that emits ultraviolet rays. Examples of the light source include a light source element, such as a light-emitting diode (LED) and a laser diode, an excimer lamp, an ultraviolet lamp, and a mercury lamp. The predetermined space is a space such as a commercial institution (e.g., a residence, an office, a hospital, a lobby, a hall, or a supermarket) or an industrial institution (e.g., a factory) that is large enough to allow a person to be present and move therein. The predetermined space does not include, for example, a space the interior of which consists of only the ultraviolet irradiation area (P), such as a tanning device. The predetermined irradiation area (P) indicates an area in the predetermined space.

The irradiator (100) generates the irradiation area (P) irradiated with ultraviolet rays. In the first embodiment, the irradiator (100) is installed on the ceiling of a building (B1) to emit ultraviolet rays from the ceiling into a room (R), thereby generating the irradiation area (P) in the room (R).

The detectors (200) each detect a target person. The detectors (200) each include, for example, at least one of a motion sensor (201), a seating sensor (202), or a terminal (203) (personal computer (PC)).

The motion sensor (201) senses the inside of the irradiation area (P) as a target region. When the target person enters the irradiation area (P), the target person is detected by the motion sensor (201). As a result, a determiner (341) of a controller (340) determines that the target person is present in the irradiation area (P).

A chair (G) and a desk (E) are set up in the irradiation area (P). The seating sensor (202) is set up on the chair (G). When the target person enters the irradiation area (P) and seats himself/herself in the chair (G), the target person is sensed by the seating sensor (202). As a result, the determiner (341) of the controller (340) determines that the target person is present in the irradiation area (P).

The terminal (203) is set up on the desk (E). When the target person enters the irradiation area (P) and starts the terminal (203), the start information on the terminal (203) is output to the controller (340). As a result, the determiner (341) of the controller (340) determines that the target person is present in the irradiation area (P).

The processing device (300) is a device for effectively achieving air sterilization (sterilization of air) by ultraviolet rays while keeping the amount of exposure of the target person to ultraviolet rays from exceeding a predetermined permissible amount.

The processing device (300) includes a first communication unit (310), a second communication unit (320), a storage (330), and the controller (340).

The first communication unit (310) is communicably connected to the irradiator (100) in a wired or wireless manner. The second communication unit (320) is communicably connected to the detectors (200) in a wired or wireless manner. Each of the first and second communication units (310) and (320) includes, for example, at least one of a device for performing wireless communication (e.g., Bluetooth (registered trademark), wireless fidelity (Wi-Fi) (registered trademark), or Internet communications) (such as a wireless LAN module) or a device for performing wired communication (such as a communication port connected to a communication cable).

The storage (330) includes a main memory (e.g., a semiconductor memory), such as a flash memory, a read only memory (ROM), and a random access memory (RAM), and may further include an auxiliary memory (e.g., a hard disk drive, a solid state drive (SSD), a secure digital (SD) memory card, or a universal seral bus (USB) flash memory). The storage (330) stores various computer programs executable by the controller (340).

The storage (330) stores irradiation area information (331), the total exposure amount (332), the total irradiation amount (333), the permissible amount (334), a target amount (335), and a learning model (336).

The irradiation area information (331) indicates the position of the ultraviolet irradiation area (P) irradiated by the irradiator (100). Examples of the irradiation area information (331) include the latitude and longitude of the ultraviolet irradiation area (P).

The total exposure amount (332) indicates the total amount of exposure of the target person to ultraviolet rays. The amount of exposure of the target person to ultraviolet rays is expressed by, for example, the product of the exposure time of the target person being exposed to ultraviolet rays from the irradiator (100) and the irradiation intensity (UV illuminance) of ultraviolet rays to which the target person is exposed (amount of exposure of target person to ultraviolet rays $(mj/cm^2)$=exposure time $(s) \times$ irradiation intensity $(W/cm^2)$).

While the irradiator (100) irradiates the irradiation area (P) with ultraviolet rays, the total exposure amount (332) stored in the storage (330) increases with increase in the time of the target person staying in the irradiation area (P). The total exposure amount (332) stored in the storage (330) is reset to 0 every first predetermined period (e.g., every day), and counting is started from 0 every time it is reset.

The total irradiation amount (333) is information indicating the total ultraviolet irradiation amount of the irradiation area (P). The ultraviolet irradiation amount is expressed by, for example, the product of the irradiation time of the irradiator (100) irradiating the irradiation area (P) with ultraviolet rays and the irradiation intensity of ultraviolet rays emitted from the irradiator (100) during the irradiation time (ultraviolet irradiation amount $(mj/cm^2)$=irradiation time $(s) \times$ irradiation intensity $(W/cm^2)$).

The total irradiation amount of ultraviolet rays increases with increase in the time of the irradiator (100) irradiating the irradiation area (P) with ultraviolet rays. The total amount of ultraviolet rays emitted that is stored in the storage (330) is reset to 0 every second predetermined period (e.g., every day), and counting is started from 0 every time it is reset.

Note that the first predetermined period (the timing at which the total exposure amount (332) is reset) and the second predetermined period (the timing at which the total irradiation amount (333) is reset) may be the same or may be different from each other.

The permissible amount (334) is information indicating the upper limit (a predetermined upper limit amount) of the total amount of exposure of the target person to ultraviolet rays. The predetermined upper limit amount is set in consideration of, for example, safety for a human body. The predetermined upper limit amount is set to, for example, 22 $mj/cm^2$. Note that the predetermined upper limit amount may vary depending on the wavelength of ultraviolet rays emitted from the irradiator (100).

The target amount (335) is information indicating the target total amount (predetermined target amount) of irradiation of the irradiation area (P) with ultraviolet rays. The predetermined target amount is set to enable effective air sterilization in the irradiation area (P), for example.

The learning model (336) indicates a control program for the irradiator (100) configured so that the total amount of irradiation of the irradiation area (P) with ultraviolet rays exceeds the predetermined target amount while the total amount of exposure of the target person to ultraviolet rays does not exceed the predetermined upper limit amount.

The controller (340) includes a processor, such as a central processing unit (CPU) or a microprocessor unit (MPU). The controller (340) executes a computer program stored in the storage (330) so as to control elements of the processing device (300). The controller (340) includes the determiner (341), an exposure amount output unit (342), a total exposure amount output unit (343), an irradiation amount output unit (344), a total irradiation amount output unit (345), a control unit (346), and a learning unit (347). The controller (340) executes a computer program stored in the storage (330) to function as the determiner (341), the exposure amount output unit (342), the total exposure amount output unit (343), the irradiation amount output unit (344), the total irradiation amount output unit (345), the control unit (346), and the learning unit (347).

The control unit (346) controls the irradiator (100) based on the amount of exposure of the target person to ultraviolet rays. The control unit (346) controls the irradiator (100) by transmitting a signal from the first communication unit (310)

to the irradiator (100). The control unit (346) controls the irradiator (100) so that ultraviolet rays of a predetermined irradiation intensity are emitted from the irradiator (100) for a predetermined time, thereby performing first to sixth irradiation processes to be described later (see FIGS. 5, 6, 9, and 11).

The irradiator (100) may be controlled using artificial intelligence (AI). In this case, the learning unit (347) generates the learning model (336) by machine learning using information on the target person and ultraviolet rays as input data. The information on the target person and ultraviolet rays includes identification information for identifying the target person, positional information on the target person, information indicating the irradiation intensity of the ultraviolet rays emitted from the irradiator (100), and information indicating an ultraviolet irradiation area (P). In the learning model (336), a control value for the irradiator (100) is used as output data. The control value for the irradiator (100) includes the irradiation intensity and/or the irradiation time of ultraviolet rays emitted from the irradiator (100). If the AI is used to control the irradiator (100), the learning model (336) can be generated so that, based on the information on the target person and ultraviolet rays, the area where the target person will be present in the future is estimated and then emission of ultraviolet rays from the irradiator (100) is controlled.

For the AI processing of the learning unit (347), deep learning technology, reinforcement learning, deep reinforcement learning, and other technologies can be used. If the AI is used to control the irradiator (100), the control unit (346) controls the irradiator (100) by using the learning model (336) generated by the learning unit (347).

The learning unit (347) generates the learning model (336) obtained by learning the control value for the irradiator (100) corresponding to the information on the target person and ultraviolet rays by, for example, a reinforcement learning method. The generated learning model (336) is stored in the storage (330). The reinforcement learning is a method in which the cycle where while the current state of an environment where a target to be learned is present (i.e., input) is observed, a predetermined action (i.e., output) is executed in the current state and some reward is given for the action is repeated through trial and error to learn a policy that maximizes the total reward as an optimal solution. In the first embodiment, the optimal solution for an operation of the irradiator (100), specifically, the irradiation intensity and/or the irradiation time of ultraviolet rays emitted from the irradiator (100) are learned. Examples of the method for reinforcement learning include Q-learning. In the Q-learning performed by the learning unit (347), the reward can be positive (plus), for example, if the amount of exposure of the target person to ultraviolet rays does not exceed the predetermined upper limit amount within the first predetermined period, and the amount of irradiation of the irradiation area (P) with ultraviolet rays from the irradiator (100) is greater than or equal to the predetermined target amount within the second predetermined period. On the other hand, the reward can be negative (minus) if the amount of exposure of the target person to ultraviolet rays exceeds the predetermined upper limit amount within the first predetermined period, or if the amount of irradiation of the irradiation area (P) with ultraviolet rays from the irradiator (100) is not greater than or equal to the predetermined target amount within the second predetermined period.

Figure 3:
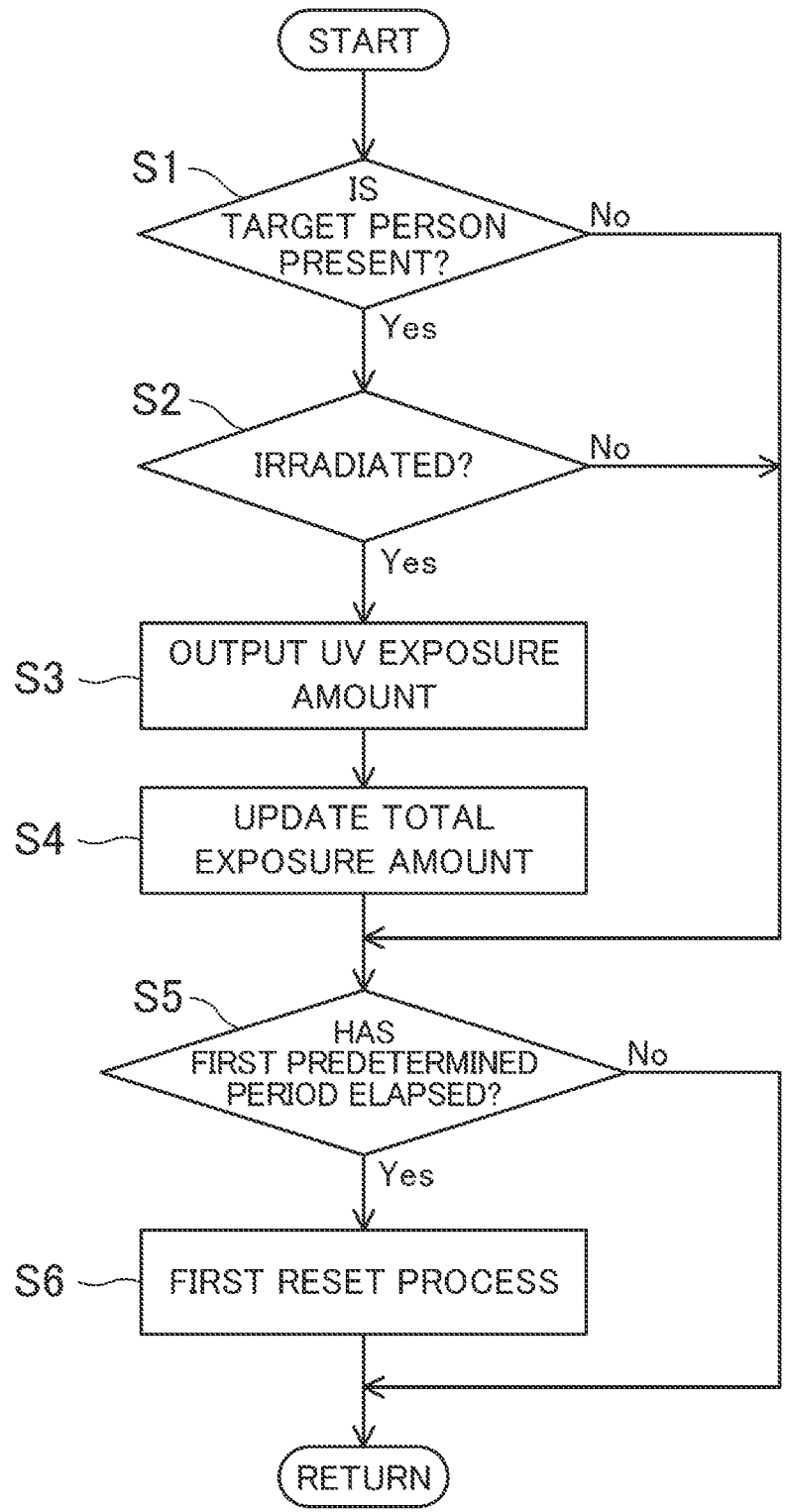
FIG. 3 is a flowchart showing a process of updating the total exposure amount.

The process of updating the total exposure amount (332) will be described with reference to FIGS. 1 to 3. FIG. 3 is a flowchart showing the process of updating the total exposure amount (332). The process of updating the total exposure amount (332) is a process in which every time the target person is exposed to ultraviolet rays emitted from the irradiator (100), the total exposure amount (332) stored in the storage (330) is updated.

As illustrated in FIGS. 1 to 3, in step S1, the determiner (341) performs a determination process of determining whether or not the target person is present in the irradiation area (P). The determiner (341) performs the determination process using the detectors (200). In the first embodiment, to perform the determination process, at least one of the motion sensor (201), the seating sensor (202), or start information on the terminal (203) is used.

If the determiner (341) determines that the target person is present in the irradiation area (P) (Yes in step S1), the process proceeds to step S2. If the determiner (341) determines that the target person is not present in the irradiation area (P) (No in step S1), the process proceeds to step S5.

In step S2, the determiner (341) determines whether or not the irradiator (100) irradiates the irradiation area (P) with ultraviolet rays. If the determiner (341) determines that the irradiation area (P) is irradiated with ultraviolet rays (Yes in step S2), the process proceeds to step S3. If the determiner (341) determines that the irradiation area (P) is not irradiated with ultraviolet rays (No in step S2), the process proceeds to step S5.

In step S3, the exposure amount output unit (342) outputs the amount of exposure of the target person to ultraviolet rays based on the determination result of the determiner (341) and operation information on the irradiator (100).

A procedure in which the exposure amount output unit (342) outputs the amount of exposure of the target person to ultraviolet rays will be described.

First, the exposure amount output unit (342) outputs the time for which the target person has stayed in the irradiation area (P) (irradiation area stay time). The irradiation area stay time is the time for which the determiner (341) has determined the target person is present in the irradiation area (P).

Next, the exposure amount output unit (342) outputs, as the time of the target person being exposed to ultraviolet rays, the time where the irradiation area stay time of the target person and the irradiation time of ultraviolet rays emitted from the irradiator (100) overlap each other. The irradiation time of ultraviolet rays emitted from the irradiator (100) is a first example of operation information on the irradiator (100) of the present invention.

Next, the exposure amount output unit (342) outputs the product of the time of the target person being exposed to ultraviolet rays and the irradiation intensity of ultraviolet rays from the irradiator (100), as the amount of exposure of the target person to ultraviolet rays. The irradiation intensity of ultraviolet rays from the irradiator (100) is a second example of the operation information on the irradiator (100) of the present invention.

In step S4, the control unit (346) adds the amount of exposure of the target person to ultraviolet rays that is output in step S3 to the total exposure amount (332) of the target person to ultraviolet rays that is stored in the storage (330). As a result, the total exposure amount (332) is updated.

In step S5, the determiner (341) determines whether or not the first predetermined period has elapsed since implementation of the last first reset process. If the determiner (341) determines that the first predetermined period has elapsed (Yes in step S5), the process proceeds to step S6. If the determiner (341) determines that the first predetermined period has not elapsed (No in step S5), the process proceeds to step S1.

In step S6, the control unit (346) performs a first reset process. The first reset process is a process in which the total exposure amount (332) of the target person to ultraviolet rays that is stored in the storage (330) is set to 0. When the process shown in step S6 is completed, the process proceeds to step S1.

Figure 4:
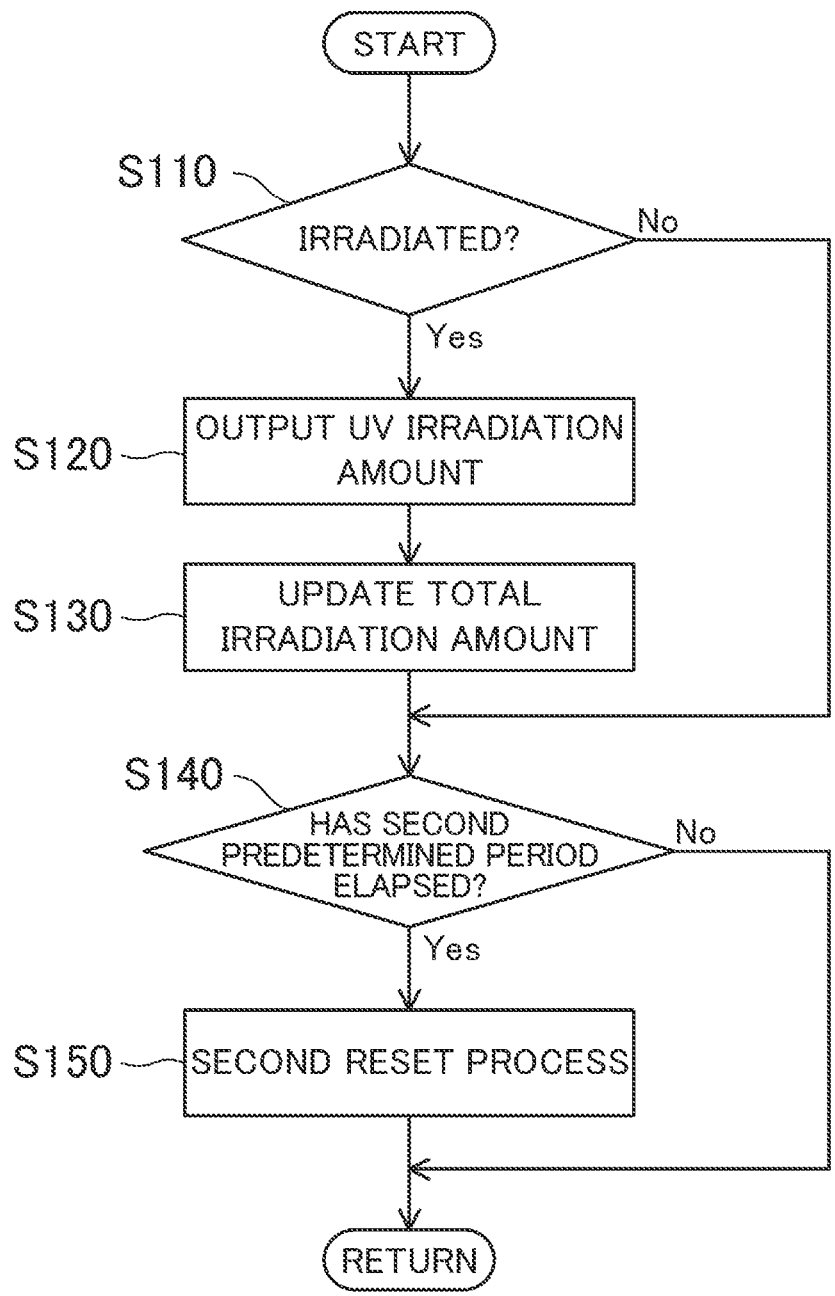
FIG. 4 is a flowchart showing a process of updating the total irradiation amount.

Next, the process of updating the total irradiation amount (333) will be described with reference to FIGS. 1, 2, and 4. FIG. 4 is a flowchart showing the process of updating the total irradiation amount (333). The process of updating the total irradiation amount (333) is a process in which every time the irradiator (100) irradiates the irradiation area (P) with ultraviolet rays, the total irradiation amount (333) stored in the storage (330) is updated.

As illustrated in FIGS. 1, 2, and 4, in step S110, the determiner (341) determines whether or not the irradiator (100) irradiates the irradiation area (P) with ultraviolet rays. If the determiner (341) determines that the irradiation area (P) is irradiated with ultraviolet rays (Yes in step S110), the process proceeds to step S120. If the determiner (341) determines that the irradiation area (P) is not irradiated with ultraviolet rays (No in step S110), the process proceeds to step S140.

In step S120, the control unit (346) outputs the amount of irradiation of the irradiation area (P) with ultraviolet rays based on the operation information on the irradiator (100). The control unit (346) outputs the product of the irradiation time and the irradiation intensity of ultraviolet rays emitted from the irradiator (100), as the ultraviolet irradiation amount.

In step S130, the control unit (346) adds the ultraviolet irradiation amount output in step S120 to the total irradiation amount (333) stored in the storage (330). As a result, the total irradiation amount (333) is updated.

In step S140, the determiner (341) determines whether or not the second predetermined period has elapsed since implementation of the last second reset process. If the determiner (341) determines that the second predetermined period has elapsed (Yes in step S140), the process proceeds to step S150. If the determiner (341) determines that the second predetermined period has not elapsed (No in step S140), the process proceeds to step S110.

In step S150, the control unit (346) performs a second reset process. The second reset process is a process in which the total irradiation amount (333) of ultraviolet rays that is stored in the storage (330) is set to 0. When the process shown in step S150 is completed, the process proceeds to step S110.

Figure 5:
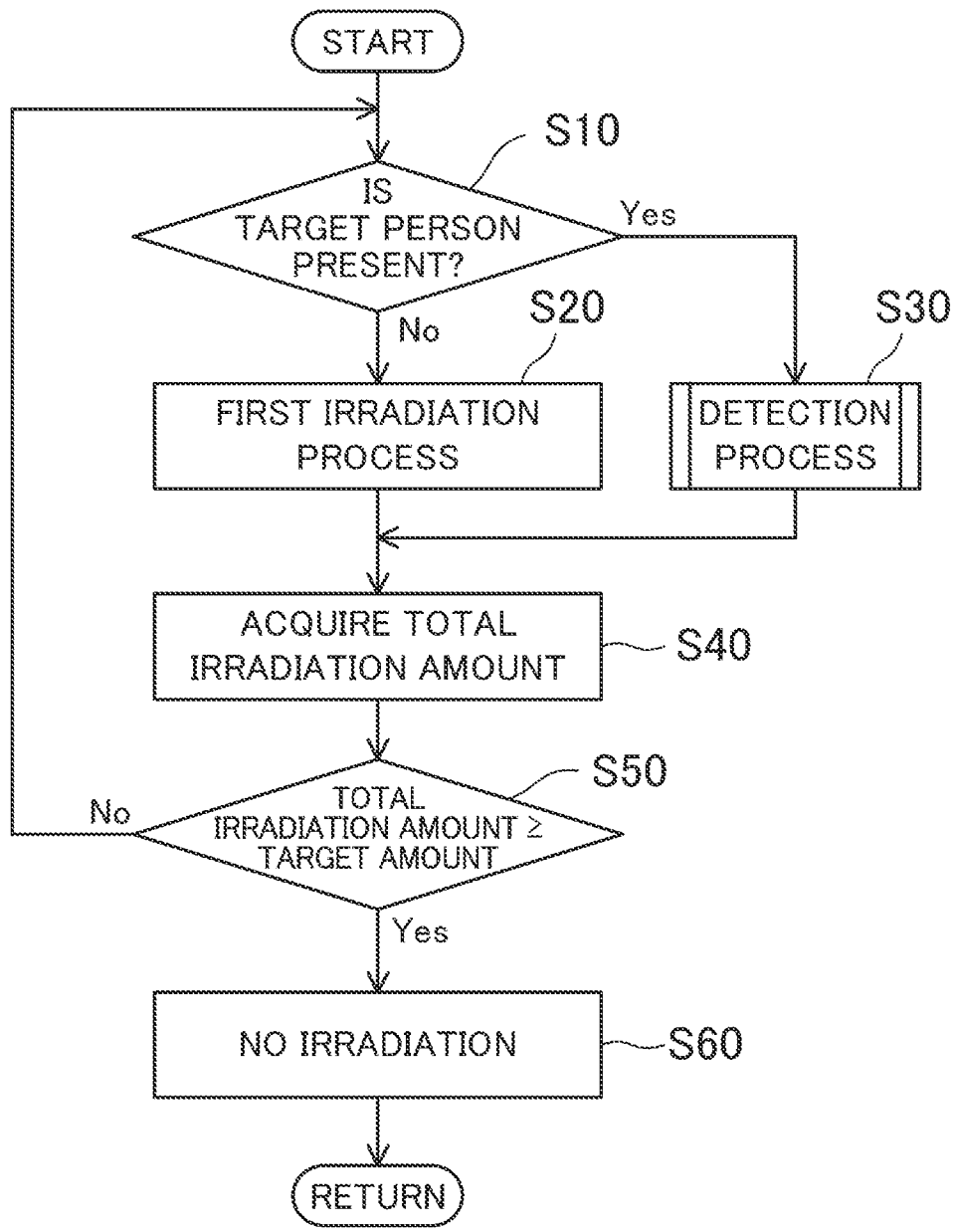
FIG. 5 is a flowchart showing a process of controlling the irradiator.

The process in which the control unit (346) controls the irradiator (100) will be described with reference to FIGS. 1, 2, and 5. FIG. 5 is a flowchart showing the process of controlling the irradiator (100). In the control process, the irradiator (100) is controlled in consideration of a balance between the amount of exposure of the target person to ultraviolet rays and the amount of irradiation of the irradiation area (P) with ultraviolet rays. The process of updating the total exposure amount (332) shown in FIG. 3 and the process of updating the total irradiation amount (333) shown in FIG. 4 are performed in parallel with the control process shown in FIG. 5.

As illustrated in FIGS. 1, 2, and 5, in step S10, the determiner (341) performs a determination process of determining whether or not the target person is present in the irradiation area (P). If the determiner (341) determines that the target person is present in the irradiation area (P) (Yes in step S10), the process proceeds to step S30. If the determiner (341) determines that the target person is not present in the irradiation area (P) (No in step S10), the process proceeds to step S20.

In step S20, the control unit (346) controls the irradiator (100) to perform a first irradiation process. The first irradiation process is a process of making the irradiator (100) emit ultraviolet rays at a predetermined first irradiation intensity. The first irradiation intensity is the irradiation intensity set to place air sterilization by ultraviolet rays at the highest priority, and is set to, for example, the irradiation intensity at full power. Then, the process proceeds to step S40.

In step S30, the control unit (346) performs a detection process. The detection process will be described later. Then, the process proceeds to step S40.

In step S40, the control unit (346) acquires the total irradiation amount (333) stored in the storage (330).

In step S50, the control unit (346) determines whether or not the total irradiation amount (333) is greater than or equal to the target amount (335) stored in the storage (330). If it is determined that the total irradiation amount (333) is greater than or equal to the target amount (335) (Yes in step S50), the process proceeds to step S60. If it is determined that the total irradiation amount (333) is not greater than or equal to the target amount (335) (No in step S50), the process proceeds to step S10.

In step S60, the control unit (346) controls the irradiator (100) so that the irradiation area (P) is not irradiated with ultraviolet rays. In this case, the operation for the irradiator (100) to emit ultraviolet rays may be turned off. In addition, for example, a light source for the irradiator (100) may be turned around so that the irradiator (100) emit ultraviolet rays in directions other than the directions toward the irradiation area (P) (e.g., directions toward the ceiling).

Figure 6:
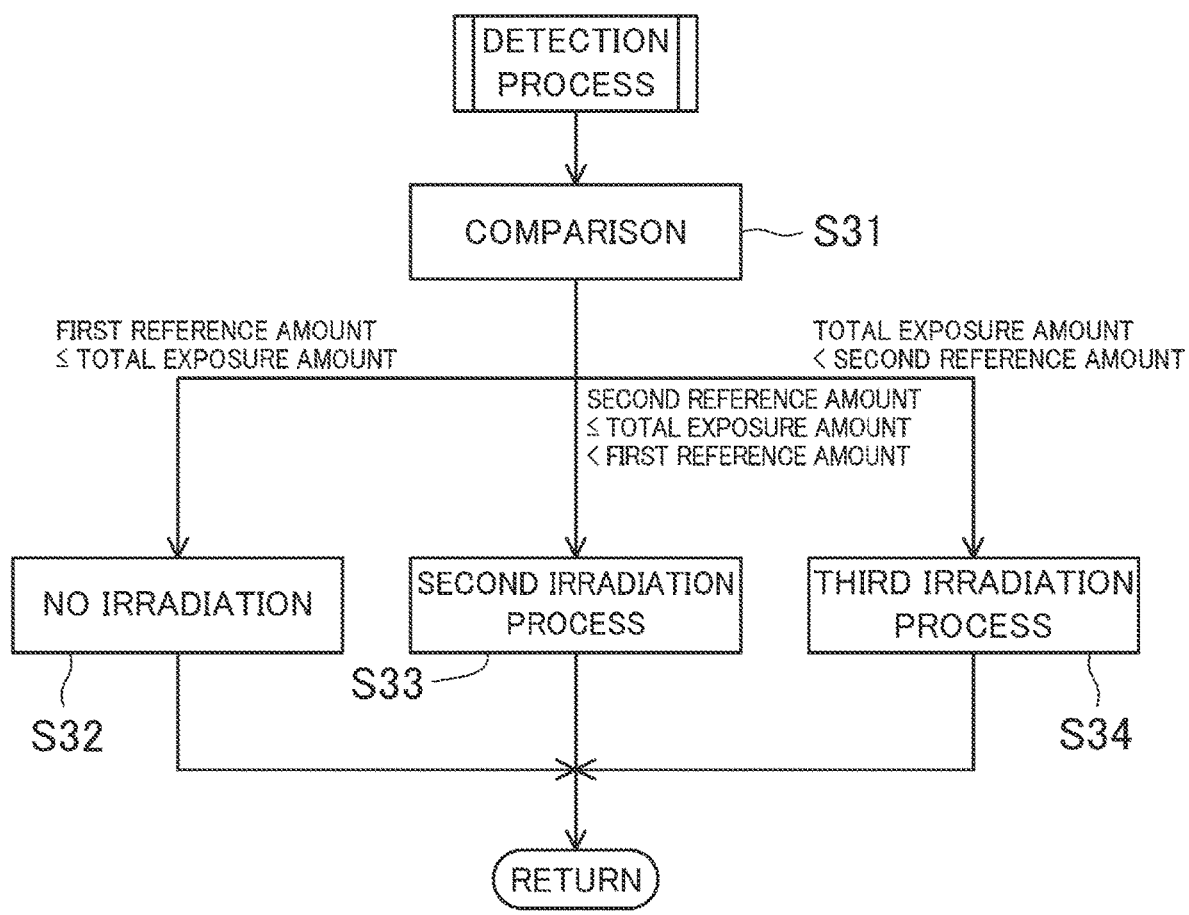
FIG. 6 is a flowchart showing a detection process.

The detection process will be described with reference to FIGS. 1, 2, 5, and 6. FIG. 6 is a flowchart showing the detection process.

As illustrated in FIGS. 1, 2, and 6, in step S31, the control unit (346) compares the total exposure amount (332) of the target person stored in the storage (330), a predetermined first reference amount, and a predetermined second reference amount to one another. Each of the first and second reference amounts indicates the ultraviolet irradiation amount. The ascending order of the first reference amount, the second reference amount, and the permissible amount (334) is the second reference amount, the first reference amount, and the permissible amount (334). Note that the first reference amount and the permissible amount (334) may be the same. If the AI is used to control the irradiator (100), each of the first and second reference amounts may be determined by machine learning.

If the total exposure amount (332) is greater than or equal to the first reference amount (first reference amount≤total exposure amount), the process proceeds to step S32. If the total exposure amount (332) is greater than or equal to the second reference amount and less than the first reference amount (second reference amount≤total exposure amount<first reference amount), the process proceeds to step S33. If the total exposure amount (332) is less than the second reference amount (total exposure amount<second reference amount), the process proceeds to step S34.

In step S32, the control unit (346) controls the irradiator (100) so that the irradiator (100) does not irradiate the irradiation area (P) with ultraviolet rays. When the process shown in step S32 is completed, the process proceeds to step S10 shown in FIG. 5.

In step S33, the control unit (346) controls the irradiator (100) to perform a second irradiation process. The second irradiation process is a process of making the irradiator (100) emit ultraviolet rays at a predetermined second irradiation intensity. The second irradiation intensity is lower than the first irradiation intensity of the ultraviolet rays emitted in the first irradiation process (see FIG. 5) in step S20 (second irradiation intensity<first irradiation intensity). The second irradiation intensity is, for example, about 20% of the first irradiation intensity. When the process shown in step S33 is completed, the process proceeds to step S10 shown in FIG. 5.

In step S34, the control unit (346) controls the irradiator (100) to perform a third irradiation process. The third irradiation process is a process of making the irradiator (100) emit ultraviolet rays at a predetermined third irradiation intensity. The third irradiation intensity is lower than the first irradiation intensity of the ultraviolet rays emitted in the first irradiation process (see FIG. 5) in step S20, and is higher than the second irradiation intensity of the ultraviolet rays emitted in the second irradiation process in step S33 (second irradiation intensity<third irradiation intensity<first irradiation intensity). The third irradiation intensity is, for example, about 50% of the first irradiation intensity. When the process shown in step S34 is completed, the process proceeds to step S10 shown in FIG. 5.

Variations of Second Irradiation Process and Third Irradiation Process

If the target person is present in the irradiation area (P) in each of the second irradiation process in step S33 and the third irradiation process in step S34 both shown in FIG. 6, the irradiation intensity of ultraviolet rays from the irradiator (100) is more limited than if the target person is not present in the irradiation area (P) (second irradiation intensity<third irradiation intensity<first irradiation intensity). This can prevent the total exposure amount (332) of the target person to ultraviolet rays (see FIG. 1) from exceeding the permissible amount (334). However, the present invention is not limited to this.

In each of the second irradiation process in step S33 and the third irradiation process in step S34, the total exposure amount (332) of the target person to ultraviolet rays (see FIG. 1) may be prevented from exceeding the permissible amount (334) by limiting the ultraviolet irradiation time and setting the irradiation intensity of ultraviolet rays from the irradiator (100) to the first irradiation intensity that is the same as in the first irradiation process (see step S20 in FIG. 5). In this case, for example, in the second irradiation process in step S33, the irradiation time of ultraviolet rays emitted from the irradiator (100) is limited to a first predetermined time, and in the third irradiation process in step S34, the irradiation time of ultraviolet rays emitted from the irradiator (100) is limited to a second predetermined time that is longer than the first predetermined time.

In each of steps S33 and S34, both the irradiation intensity of ultraviolet rays from the irradiator (100) and the ultraviolet irradiation time may be limited.

If the AI is used to control the irradiator (100), the irradiation intensity of ultraviolet rays and the ultraviolet irradiation time in each of steps S33 and S34 may be determined by machine learning.

First Variation of Detector (200)

The detectors (200) (see FIG. 1) may include an imager (such as a camera) that captures an image of the irradiation area (P). In this case, in step S1 shown in FIG. 3 and step S10 shown in FIG. 5, the second communication unit (320) receives image data captured by the imager that is the detector (200). The determiner (341) performs, for example, pattern matching between the image data received by the second communication unit (320) and the image data prepared in advance on the target person, thereby determining whether or not the target person is present in the irradiation area (P).

Second Variation of Detector (200)

The detectors (200) may be each configured as a portable terminal (such as a smartphone or a tablet PC) carried by the target person. In this case, the portable terminal includes a global positioning system (GPS) module, and acquires positional information on the target person using the GPS module. The GPS module receives radio waves from global positioning system (GPS) satellites and calculates the positional information on the target person (information indicating the latitude and longitude) from the received radio waves. The portable terminal that is the detector (200) is communicably connected to the second communication unit (320) in a wired or wireless manner. The positional information on the target person calculated by the portable terminal is transmitted to the second communication unit (320) through a communication network such as the Internet.

If the detector (200) is configured as a portable terminal, the determiner (341) determines whether or not the target person is present in the irradiation area (P), in step S1 shown in FIG. 3 and step S10 shown in FIG. 5, based on the positional information on the target person received by the second communication unit (320) and the irradiation area information (331) stored in the storage (330). If the spot indicated by the positional information on the target person is located in the area indicated by the irradiation area information (331), the determiner (341) determines that the target person is present in the irradiation area (P). If the spot indicated by the positional information on the target person is not located in the area indicated by the irradiation area information (331), the determiner (341) determines that the target person is not present in the irradiation area (P).

Advantages of First Embodiment

The control unit (346) controls the irradiator (100) based on the amount of exposure of the target person to ultraviolet rays as described above with reference to FIGS. 1 to 6. Thus, if the target person is present in the irradiation area (P), ultraviolet rays can be radiated to the irradiation area (P) with the target person reliably safe so that the total exposure amount (332) of the target person does not exceed the permissible amount (334). As a result, the irradiation area can be effectively sterilized by ultraviolet rays.

If the target person is present in the irradiation area (P), the control unit (346) controls the irradiator (100) so that the irradiation intensity of ultraviolet rays is lower than if no person is present in the irradiation area (P) (see step S20 in FIG. 5, and steps S33 and S34 in FIG. 6). Alternatively, the control unit (346) controls the irradiator so that the irradiation area is not irradiated with ultraviolet rays (see step S32 in FIG. 6). This can effectively reduce the amount of exposure of the target person to ultraviolet rays.

In addition, the irradiator (100) irradiates, with ultraviolet rays, the irradiation area (P) where the target person has stayed, and thus effective sterilization by ultraviolet rays can be performed even if bacteria that have been parasitic on the target person are spread in the irradiation area (P) during stay of the target person therein.

Second Embodiment

Figure 7:
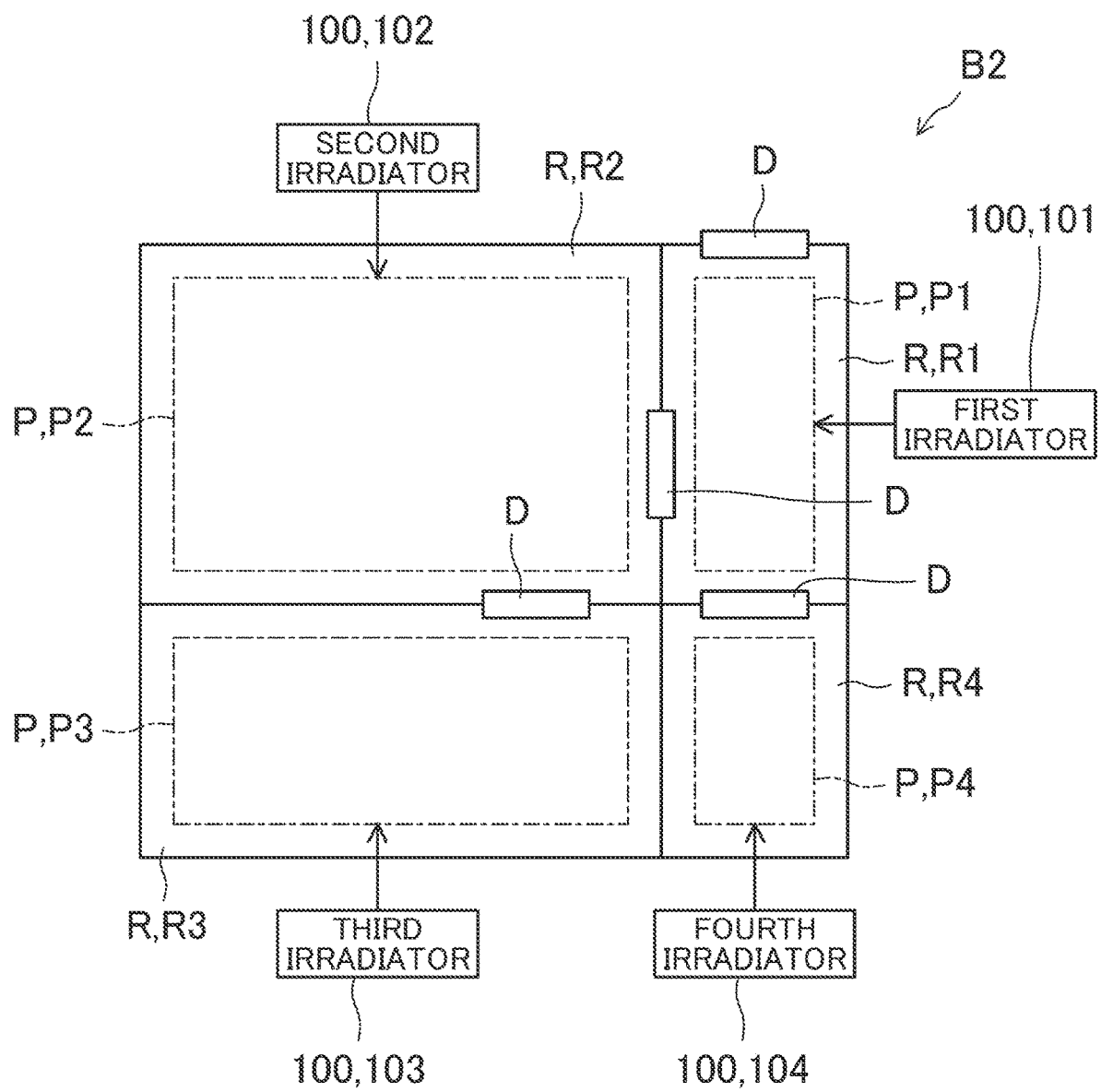
FIG. 7 illustrates a second example of installation of irradiators and detectors.

A second embodiment of a UV emission device (10) will be described with reference to FIG. 7. FIG. 7 illustrates a second example of installation of irradiators (100) and a detector (200).

As illustrated in FIG. 7, in the second embodiment, a plurality of rooms are provided in a building (B2). The internal spaces (R) (internal spaces (R1) to (R4)) of the rooms each include an irradiation area (P) (irradiation areas (P1) to (P4)) irradiated with ultraviolet rays by the irradiator (100) (first to fourth irradiators (101) to (104)). Each room has a gate through which a target person comes in and out of the room. The gate is provided with a door (D).

The plurality of internal spaces (R) (internal spaces (R1) to (R4)) are each provided with the detector (200) configured to detect the target person (at least one of a motion sensor (201), a seating sensor (202), or a terminal (203)) (see FIG. 2).

Advantages of Second Embodiment

If the plurality of irradiation areas (P) are provided as illustrated in FIG. 7, the controller (340) performs the process of updating the total exposure amount (332) shown in FIG. 3, the process of updating the total irradiation amount (333) shown in FIG. 4, and the control processes illustrated in FIGS. 5 and 6, for each of the irradiation areas (P). As a result, the amount of exposure of the target person to ultraviolet rays can be reduced while a sufficient amount of irradiation of the plurality of irradiation areas (P) (irradiation areas (P1) to (P4)) with ultraviolet rays can be secured.

In addition, the control unit (346) controls the irradiator (100) so that ultraviolet rays are emitted without emission to an area where the target person is present (one of the irradiation areas (P) where the target person is present) (see step S20 in FIG. 5 and step S32 in FIG. 6). As a result, the amount of exposure of the target person to ultraviolet rays can be effectively reduced.

Variation of Second Embodiment

In the second embodiment, the plurality of rooms are provided, and each of them includes an irradiation area (P) (any one of the irradiation areas (P1) to (P4)). However, the present invention is not limited to this. A plurality of regions without overlapping each other may be set in one room so that each of the set regions includes an irradiation area (P).

Third Embodiment

A third embodiment of a UV emission device (10) will be described with reference to FIGS. 1 and 8.

Figure 8:
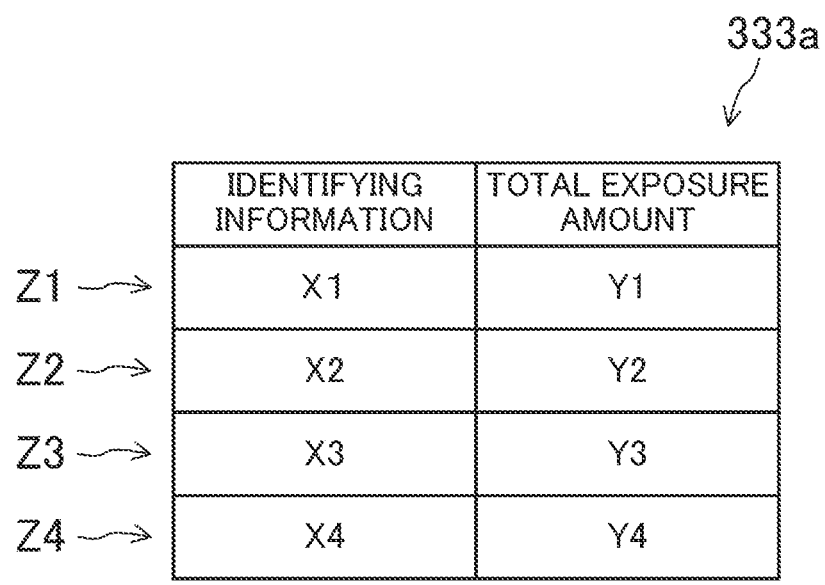
FIG. 8 shows a total irradiation amount group that is a variation of the total irradiation amount.

As shown in FIG. 8, in the third embodiment, there exist a plurality of target persons (first to fourth target persons (Z1) to (Z4)). The plurality of target persons (first to fourth target persons (Z1) to (Z4)) correspond to a plurality of pieces of identification information (first to fourth identification information (X1) to (X4)), respectively. The plurality of target persons are identified by the corresponding pieces of identification information.

FIG. 8 shows a total irradiation amount group (333a) that is a variation of the total irradiation amount (333) (see FIG. 1). The total irradiation amount group (333a) is information indicating associations between the plurality of pieces of identification information (the first to fourth identification information (X1) to (X4)) and a plurality of total exposure amounts (first to fourth exposure amounts (Y1) to (Y4)). The total irradiation amount group (333a) includes information indicating the total exposure amount of each of the target persons. The total irradiation amount group (333a) is stored in the storage (330).

As shown in FIGS. 1 and 8, in the third embodiment, detectors (200) (see FIG. 1) include, for example, an imager that captures an image of an irradiation area (P).

In the third embodiment, just like the first embodiment, the controller (340) performs the process of updating the total exposure amount (332) shown in FIG. 3, the process of updating the total irradiation amount (333) shown in FIG. 4, and the control processes respectively shown in FIGS. 5 and 6. In this case, the controller (340) performs the process of updating the total exposure amount (332) and the control process for each of the target persons.

The process of updating the total exposure amount (332) according to the third embodiment will be described with reference to FIG. 3. Differences from the updating process of the first embodiment will be mainly described below.

As shown in FIG. 3, if it is determined in step S1 that the target person is present in the irradiation area (P), the determiner (341) identifies the target person present in the irradiation area (P). The target person is identified such that it is determined as to which of the plurality of target persons (first to fourth target persons (Z1) to (Z4)) the target person present in the irradiation area (P) corresponds to. In this case, the imager captures an image of the target person in the irradiation area (P). Then, the determiner (341) executes, for example, pattern matching between data of the captured image of the target person and the data of images of the target persons prepared in advance, thereby identifying the target person whose image has been captured. In other words, the target person whose image has been captured by the imager is the target person present in the irradiation area (P).

In step S3, the exposure amount output unit (342) associates and outputs the identification information on the target person determined in step S1 with the amount of exposure of the target person to ultraviolet rays. For example, if it is determined in step S1 that the target person is the first target person (Z1), the exposure amount output unit (342) associates and outputs the first identification information (X1) on the first target person (Z1) with the amount of exposure of the first target person (Z1) to ultraviolet rays.

In step S4, the control unit (346) adds the ultraviolet exposure amount output in step S3 to the total exposure amount of the target person determined in step S1 included in the total irradiation amount group (333a) stored in the storage (330). As a result, the total exposure amount is updated.

For example, if it is determined in step S1 that the target person is the first target person (Z1), the control unit (346) adds the ultraviolet exposure amount output in step S3 to the first total exposure amount (Y1) of the first target person (Z1). As a result, the first total exposure amount (Y1) of the first target person (Z1) is updated.

The control process (see FIG. 5) according to the third embodiment will be described with reference to FIGS. 5 and 6. Differences from the first embodiment will be mainly described below.

If, as shown in FIG. 5, in step S10, the determiner (341) determines that at least one of the plurality of target persons (the first to fourth target persons (Z1) to (Z4)) is present in the irradiation area (P) (Yes in step S10), the process proceeds to step S30. As a result, a detection process (see FIG. 6) is performed in step S30.

If the determiner (341) determines that none of the target persons are present in the irradiation area (P) (No in step S10), the process proceeds to step S20. As a result, a first irradiation process is performed in step S20.

First Variation of Process For Identifying Plurality of Target Persons

In the third embodiment, the determiner (341) identifies the target persons by pattern matching using image data on the target persons. However, the present invention is not limited to this. For example, each target person may carry a portable object (such as a card) including an identifier (such as a QR code (registered trademark)) assigned to the target person. The identifier of each target person and the identification information (first to fourth identification information (X1) to (X4)) are associated with each other. In this case, if a target person is present in the irradiation area (P), the imager that is the detector (200) captures an image of the identifier carried by the target person. Information indicating the identifier whose image has been captured by the imager is transmitted to the second communication unit (320). Then, the determiner (341) identifies the target person present in the irradiation area (P) from the identifier received by the second communication unit (320).

Second Variation of Process For Identifying Plurality of Target Persons

In a second variation, a plurality of target persons each carry a portable terminal, which is configured to transmit positional information on the target person carrying the portable terminal (see the second variation of the detector (200) of the first embodiment). Identification information on the target person carrying the portable terminal is added to the positional information. For example, positional information on the first target person (Z1) and a first identification information (X1) on the first target person (Z1) are transmitted from the portable terminal carried by the first target person (Z1). As a result, the determiner (341) can identify the target persons from the identification information transmitted together with the positional information.

Advantages of Third Embodiment

As described with reference to FIGS. 5 and 6, the exposure amount output unit (342) associates and outputs the identification information on each target person with the amount of exposure of the target person to ultraviolet rays. As a result, the ultraviolet exposure amount of each of the plurality of target persons (first to fourth target persons (Z1) to (Z4)) can be output with identification secured.

Fourth Embodiment

Figure 9:
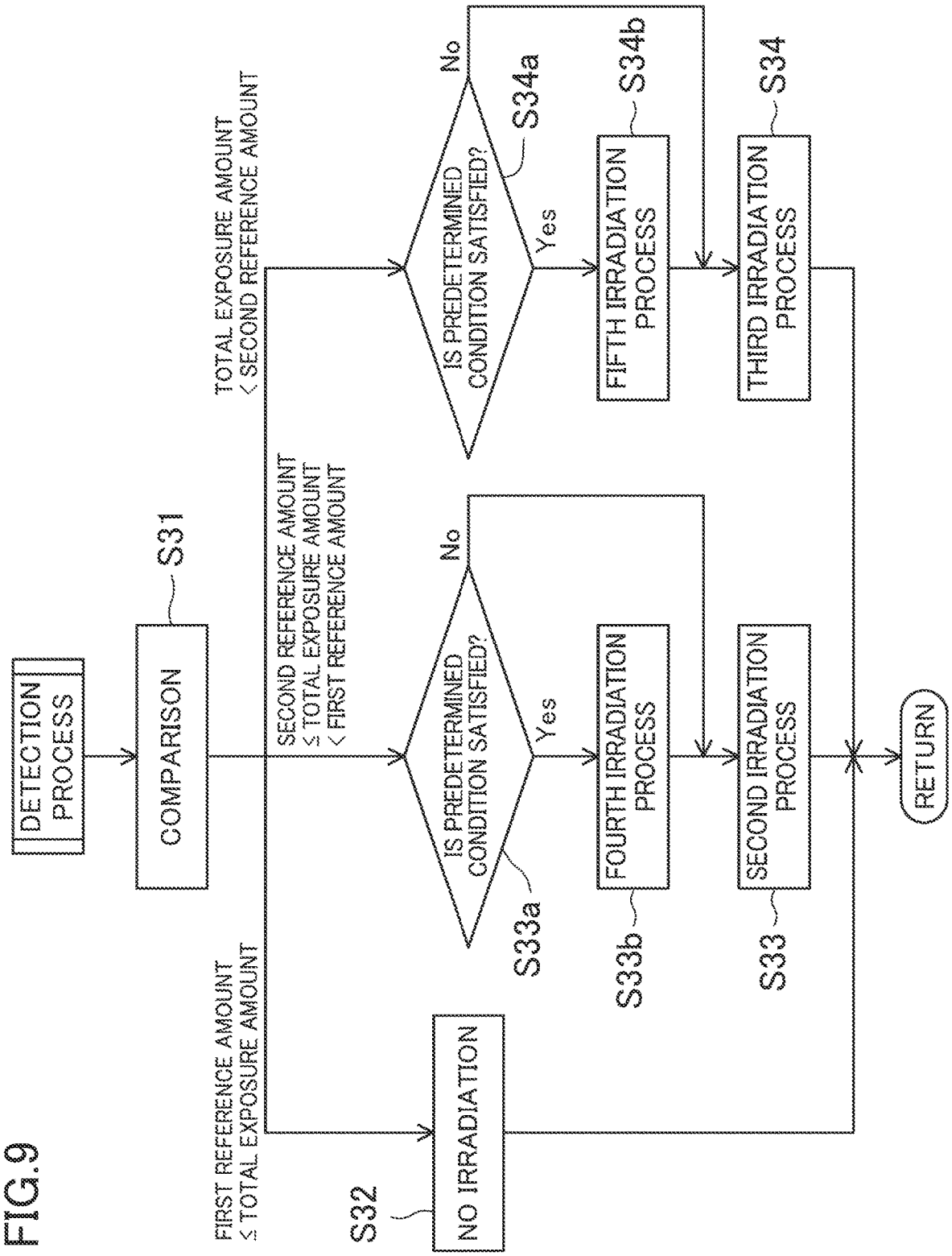
FIG. 9 is a flowchart showing a variation of the detection process.

A fourth embodiment of a UV emission device (10) will be described with reference to FIGS. 1 and 9. FIG. 9 is a flowchart showing a variation of the detection process (see FIG. 6).

In the fourth embodiment, a plurality of people in addition to a target person are present. In addition, in the fourth embodiment, as indicated by the second variation of the process for identifying the plurality of target persons according to the third embodiment, each of the plurality of people including the target person possesses a portable terminal. The position of each person can be determined by the positional information and identification information transmitted from the associated portable terminal.

In the fourth embodiment, the process of updating the total exposure amount (332) shown in FIG. 3, the process of updating the total irradiation amount (333) shown in FIG. 4, the control process shown in FIG. 5, and the variation of the detection process shown in FIG. 9 are performed for the target person.

A variation of the detection process will be described below. Differences from the detection process shown in FIG. 6 will be mainly described below.

As shown in FIGS. 1 and 9, in step S31, the control unit (346) compares the total exposure amount (332) of the target person stored in the storage (330), a predetermined first reference amount, and a predetermined second reference amount to one another. If the total exposure amount (332) is greater than or equal to the first reference amount (first reference amount≤total exposure amount), the process proceeds to step S32. If the total exposure amount (332) is greater than or equal to the second reference amount and less than the first reference amount (second reference amount≤total exposure amount<first reference amount), the process proceeds to step S33a. If the total exposure amount (332) is less than the second reference amount (total exposure amount<second reference amount), the process proceeds to step S34a.

In step S33a, the determiner (341) determines whether or not a predetermined condition is satisfied. The predetermined condition is that the number of times of a plurality of people coming close to each other with a distance shorter than a predetermined distance within a predetermined period in the irradiation area (P) be greater than a predetermined number of times. The determiner (341) functions as a timer, and counts the predetermined period. The determiner (341) determines whether or not the predetermined condition is satisfied within the predetermined period based on positional information on each of the plurality of people transmitted from the portable terminal of each of the plurality of people.

If the determiner (341) determines that the predetermined condition is satisfied (Yes in step S33a), the process proceeds to step S33b. If the determiner (341) determines that the predetermined condition is not satisfied (No in step S33a), the process proceeds to step S33.

In step S33b, the control unit (346) controls the irradiator (100) to perform a fourth irradiation process. The fourth irradiation process is a process of controlling the irradiator (100) so that the irradiation intensity and/or the irradiation time of ultraviolet rays emitted from the irradiator (100) are greater than in the second irradiation process (see step S33). When the process shown in step S33b is completed, the process proceeds to step S33.

In step S34a, the determiner (341) determines whether or not a predetermined condition is satisfied. If the determiner (341) determines that the predetermined condition is satisfied (Yes in step S34a), the process proceeds to step S34b. If the determiner (341) determines that the predetermined condition is not satisfied (No in step S34a), the process proceeds to step S34.

In step S34b, the control unit (346) controls the irradiator (100) to perform a fifth irradiation process. The fifth irradiation process is a process of controlling the irradiator (100) so that the irradiation intensity and/or the irradiation time of ultraviolet rays emitted from the irradiator (100) are greater than in the third irradiation process (see step S34).

When the process shown in step S34b is completed, the process proceeds to step S34.

Advantages of Fourth Embodiment

As described above with reference to FIGS. 1 and 9, if the predetermined condition is satisfied in the irradiation area (P), the control unit (346) controls the irradiator (100) so that the irradiation intensity and/or the irradiation time of ultraviolet rays emitted from the irradiator (100) are greater than if the predetermined condition is not satisfied (see steps S33b, S33, 34b, and S34). If the number of times of a plurality of people coming close to each other with a distance shorter than the predetermined distance increases, the risk of infection between the people close to each other increases. However, in this case, the irradiation intensity and/or the irradiation time of ultraviolet rays are increased to enable effective sterilization by ultraviolet rays, and thus the risk of infection can be reduced.

Fifth Embodiment

Figure 10:
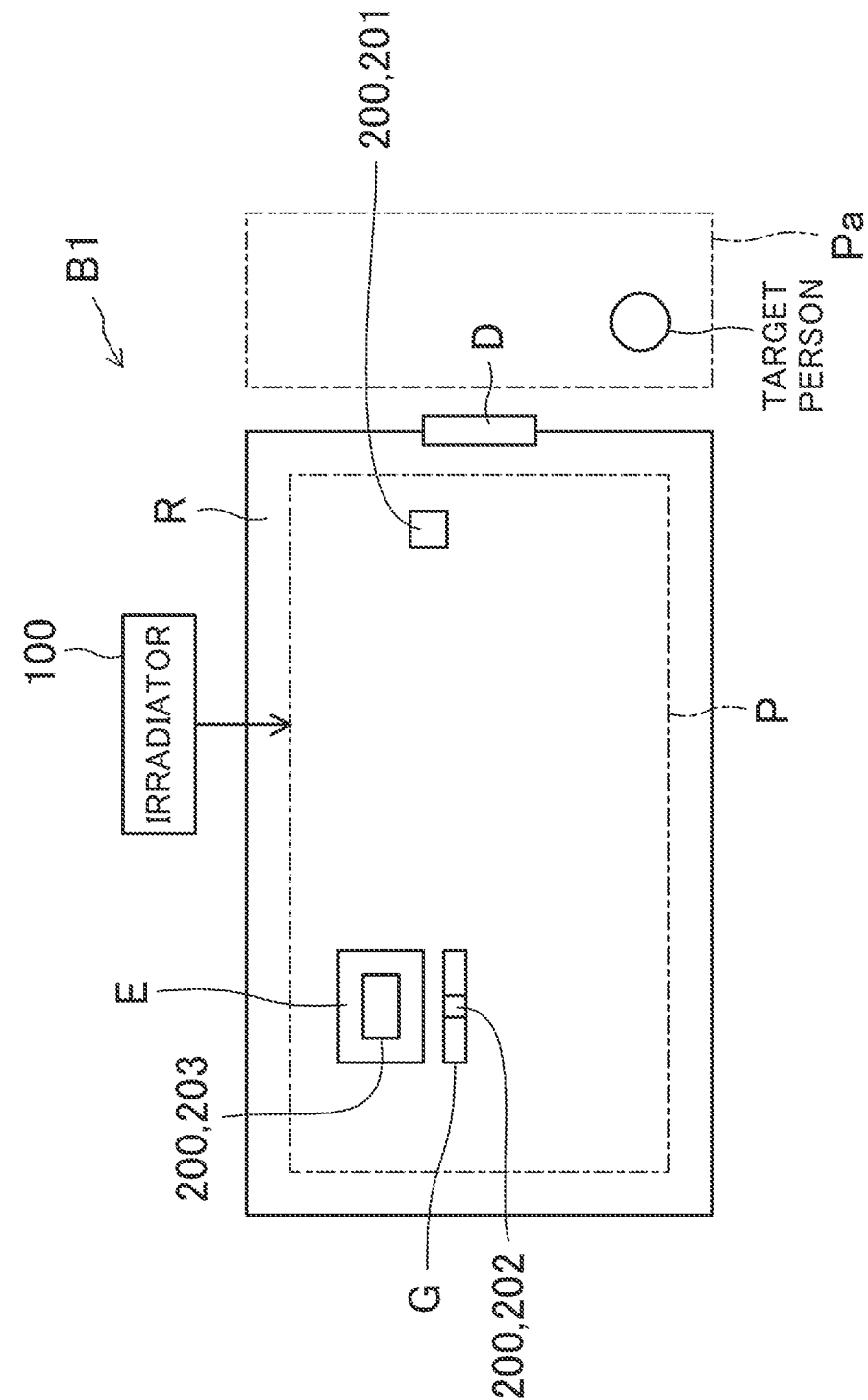
FIG. 10 illustrates a third example of installation of an irradiator and detectors.
Figure 11:
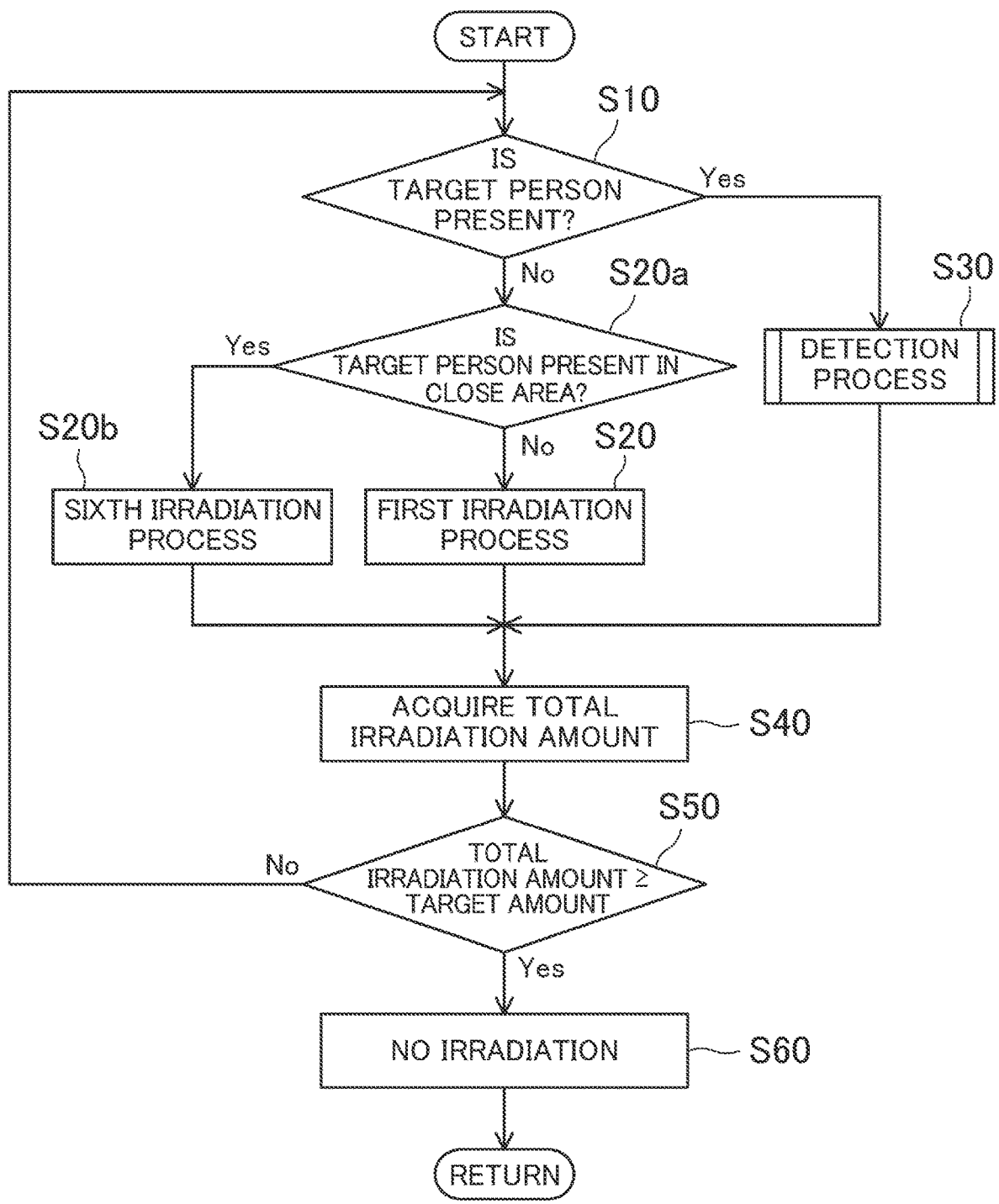
FIG. 11 is a flowchart showing a variation of the process of controlling the irradiator.

A fifth embodiment of a UV emission device (10) will be described with reference to FIGS. 1, 10, and 11. FIG. 10 illustrates a third example of installation of an irradiator (100) and detectors (200). FIG. 11 is a flowchart showing a variation of the process of controlling the irradiator (100) illustrated in FIG. 5.

As illustrated in FIG. 10, in the fifth embodiment, a close area (Pa) close to an irradiation area (P) is set. The close area (Pa) is, for example, an area located within a predetermined distance from the irradiation area (P) through a passage that communicates with the irradiation area (P) (in the fifth embodiment, a gate opened and closed by a door (D)).

As illustrated in FIGS. 1 and 10, in the fifth embodiment, the detectors (200) further include a close-area appliance configured to detect a target person present in the close area (Pa), such as a motion sensor that senses a target region in the close area (Pa), a seating sensor provided in the close area (Pa), a terminal provided in the close area (Pa), and an imager configured to capture an image of the close area (Pa).

A variation of the process of controlling the irradiator (100) will be described with reference to FIGS. 1, 10, and 11. Differences from the control process illustrated in FIG. 4 will be mainly described below.

As illustrated in FIGS. 1, 10, and 11, if the determiner (341) determines in step S10 that the target person is not present in the irradiation area (P) (No in step S10), the process proceeds to step S20a.

In step S20a, the determiner (341) determines whether or not the target person is present in the close area (Pa) by using the close-area appliance of the detector (200). The determiner (341) may determine whether or not the target person is present in the close area (Pa) by using positional information on the target person transmitted from the portable terminal of the target person.

If the determiner (341) determines that the target person is present in the close area (Pa) (Yes in step S20a), the process proceeds to step S20b. If the determiner (341) determines that the target person is not present in the close area (Pa) (No in step S20a), the process proceeds to step S20.

In step S20b, the control unit (346) controls the irradiator (100) to perform a sixth irradiation process. The sixth irradiation process is a process of controlling the irradiator (100) so that the irradiation intensity of ultraviolet rays is lower than in the first irradiation process (see step S20).

When the process shown in step S20b is completed, the process proceeds to step S40.

Advantages of Fifth Embodiment

As described above with reference to FIGS. 1, 10, and 11, if the determiner (341) determines that the target person is present in the close area (Pa), the control unit (346) controls the irradiator (100) so that the irradiation intensity of ultraviolet rays is lower than if the target person is present outside both the irradiation area (P) and the close area (Pa) (see steps S20 and S20b). Thus, the irradiation intensity of ultraviolet rays emitted to the irradiation area (P) can be set lower in consideration of the situation where the target person present in the close area (Pa) can easily enter the irradiation area (P).

Other Embodiments

While the embodiments and variations thereof have been described above, it will be understood that various changes in form and details may be made without departing from the spirit and scope of the claims (e.g., (1) to (2)). The embodiments and the variations thereof may be combined and replaced with each other without deteriorating intended functions of the present disclosure.

(1) The UV emission device (10) may be provided in an air conditioner.
(2) As shown in steps S33 and S34 shown in FIGS. 6 and 9 and steps S33b and S34b shown in FIG. 9, if the irradiation area (P) where the target person is present is irradiated with ultraviolet rays, a wavelength filter or any other element maybe used to reduce or remove hazardous components.

As can be seen from the foregoing description, the present disclosure is useful for a processing device, a UV emission device, and a UV emission method.

The invention claimed is:
1. A UV emission device comprising:
an irradiator that irradiates a predetermined irradiation area in a predetermined space with ultraviolet rays in accordance with a stored total exposure amount of an identified target person; and
a processing device that
controls the irradiator based on the stored total exposure amount of the identified target person to ultraviolet rays;
performs a determination process of determining whether or not a target person is present in the irradiation area, the determiner identifying the target person determined to be present in the irradiation area as the identified target person;
outputs an amount of exposure of the identified target person to ultraviolet rays based on a determination result of the determiner and operation information on the irradiator; and
adds the amount of exposure of the ultraviolet rays to the stored total exposure amount of ultraviolet rays in order to provide an updated stored total exposure amount, so as to control the irradiator such that,
in a case where the irradiation area in which the identified target person is present is irradiated with ultraviolet rays, the processing device controls the irradiator so as to limit an irradiation intensity of ultraviolet rays, so as to limit an irradiation time of ultraviolet rays while keeping the irradiation intensity of ultraviolet rays at a same level, or so as to limit both the irradiation intensity of ultraviolet rays and the irradiation time of ultraviolet rays, as compared to a case where the irradiation area in which the identified target person is not present is irradiated with ultraviolet rays, thereby controlling the irradiator so that the updated stored total exposure amount of the identified target person to ultraviolet rays is less than or equal to a predetermined permissible amount.

2. The UV emission device of claim 1, wherein the processing device controls at least one of an irradiation intensity and an irradiation time of ultraviolet rays emitted from the irradiator.

3. The UV emission device of claim 1, wherein if the identified target person is present in the irradiation area, the processing device controls the irradiator
   so that an irradiation intensity of ultraviolet rays is lower than if no person is present in the irradiation area or
   so that the irradiation area is not irradiated with ultraviolet rays.

4. The UV emission device of claim 1, wherein the processing device controls the irradiator so that ultraviolet rays are emitted without emission to an area where the identified target person is present.

5. The UV emission device of claim 1, wherein if a condition that the number of times of a plurality of people coming close to each other with a distance shorter than a predetermined distance within a predetermined period in the irradiation area is greater than a predetermined number of times is satisfied,
   the processing device controls the irradiator so that at least one of an irradiation intensity and an irradiation time of ultraviolet rays emitted from the irradiator is greater larger than if the condition is not satisfied.

6. The UV emission device of claim 1, wherein the processing device controls the irradiator so that the irradiation area where the identified target person has stayed is irradiated with ultraviolet rays.

7. The UV emission device of claim 1, wherein the processing device performs the determination process using at least one of
   a motion sensor that senses a target region in the irradiation area,
   a seating sensor provided in the irradiation area, and start information on a terminal provided in the irradiation area.

8. The UV emission device of claim 1, wherein the processing device associates and outputs identification information on the identified target person with the amount of exposure of the identified target person to ultraviolet rays.

9. The UV emission device of claim 1, wherein the processing device determines whether or not the identified target person is present in a close area close to the irradiation area, and
   if the processing device determines that the identified target person is present in the close area (Pa), the processing device controls the irradiator so that an irradiation intensity of ultraviolet rays is lower than if the identified target person is present outside both the irradiation area and the close area.

10. The UV emission device of claim 1, wherein the processing device controls the irradiator using information on the identified target person and ultraviolet rays as input data.

11. The UV emission device of claim 10, wherein the information on the identified target person and ultraviolet rays includes
    identification information for identifying the identified target person,
    positional information on the identified target person,
    information indicating an irradiation intensity of ultraviolet rays emitted from the irradiator, and
    information indicating the irradiation area.

12. The UV emission device of claim 1, wherein the ultraviolet rays emitted from the irradiator have a wavelength
    greater than or equal to 190 nm and
    less than or equal to 280 nm.

13. A processing device comprising:
    the processing device that
    communicates with an irradiator that irradiates a predetermined irradiation area in a predetermined space with ultraviolet rays in accordance with a stored total exposure amount of an identified target person;
    controls the irradiator by transmitting a signal to the irradiator;
    performs a determination process of determining whether or not a target person is present in the irradiation area, the target person determined to be present in the irradiation area being identified as the identified target person; and
    outputs an amount of exposure of the identified target person to ultraviolet rays based on a determination result and operation information on the irradiator,
    controls the irradiator based on the stored total exposure amount of the identified target person to ultraviolet rays, and
    adds the amount of exposure of the ultraviolet rays to the stored total exposure amount of ultraviolet rays in order to provide an updated stored total exposure amount, so as to control the irradiator such that,
    in a case where the irradiation area in which the identified target person is present is irradiated with ultraviolet rays, the processing device controls the irradiator so as to limit an irradiation intensity of ultraviolet rays, so as to limit an irradiation time of ultraviolet rays while keeping the irradiation intensity of ultraviolet rays at a same level, or so as to limit both the irradiation intensity of ultraviolet rays and the irradiation time of ultraviolet rays, as compared to a case where the irradiation area in which the identified target person is not present is irradiated with ultraviolet rays, thereby controlling the irradiator so that the updated stored total exposure amount of the identified target person to ultraviolet rays is less than or equal to a predetermined permissible amount.

* * * * *